United States Patent
Broom et al.

(10) Patent No.: US 9,421,169 B2
(45) Date of Patent: Aug. 23, 2016

(54) ORAL DOSAGE FORMS FOR DELIVERY OF THERAPEUTIC AGENTS

(75) Inventors: Daniel Broom, Branford, CT (US); Joshua Stopek, Guilford, CT (US)

(73) Assignee: Covidien LP, Mansfield, MA (US)

( * ) Notice: Subject to any disclaimer, the term of this patent is extended or adjusted under 35 U.S.C. 154(b) by 1081 days.

(21) Appl. No.: 12/914,345

(22) Filed: Oct. 28, 2010

(65) Prior Publication Data
US 2011/0123614 A1    May 26, 2011

Related U.S. Application Data

(60) Provisional application No. 61/262,963, filed on Nov. 20, 2009.

(51) Int. Cl.
| | |
|---|---|
| *A61K 9/20* | (2006.01) |
| *A61K 9/00* | (2006.01) |
| *A61J 3/00* | (2006.01) |
| *A61J 3/06* | (2006.01) |
| *A61J 3/07* | (2006.01) |

(52) U.S. Cl.
CPC ............. *A61K 9/2072* (2013.01); *A61K 9/0065* (2013.01); *A61J 3/005* (2013.01); *A61J 3/06* (2013.01); *A61J 3/071* (2013.01)

(58) Field of Classification Search
None
See application file for complete search history.

(56) References Cited

U.S. PATENT DOCUMENTS

| | | | |
|---|---|---|---|
| 4,207,890 A | 6/1980 | Mamajek et al. | |
| 4,758,436 A | 7/1988 | Caldwell et al. | |
| 4,767,627 A | 8/1988 | Caldwell et al. | |
| 5,167,962 A * | 12/1992 | Lew et al. | 424/426 |
| 5,516,523 A | 5/1996 | Heiber et al. | |
| 5,639,469 A | 6/1997 | Benes et al. | |
| 5,688,520 A | 11/1997 | Karsenty et al. | |
| 5,908,637 A | 6/1999 | Benes et al. | |
| 6,776,999 B1 | 8/2004 | Krumme | |
| 7,001,609 B1 | 2/2006 | Matson et al. | |
| 2004/0215171 A1 | 10/2004 | Houzego et al. | |
| 2009/0110714 A1 | 4/2009 | Boyden et al. | |

FOREIGN PATENT DOCUMENTS

| | | | |
|---|---|---|---|
| DE | 101 11 780 A1 | 10/2002 | |
| EP | 0 344 939 A2 | 12/1989 | |
| EP | 0 415 671 A2 | 3/1991 | |
| EP | 0415671 A2 * | 3/1991 | ............... A61K 9/22 |
| GB | 12117 A | 0/1915 | |

OTHER PUBLICATIONS

Sonobe (EP 0415671 published on Jun. 3, 1991).*
European Search Report for EP 10251970.9-1219 date of completion is Nov. 22, 2011 (4 pages).

* cited by examiner

*Primary Examiner* — H. Sarah Park

(57) ABSTRACT

Oral dosage forms for the delivery of therapeutic agents include mechanical fasteners for engaging tissue of the gastrointestinal tract.

20 Claims, 4 Drawing Sheets

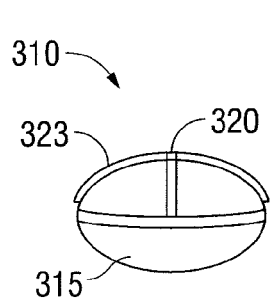
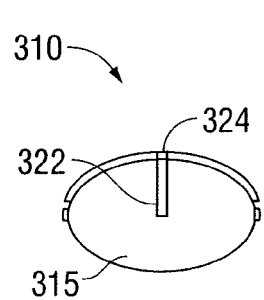
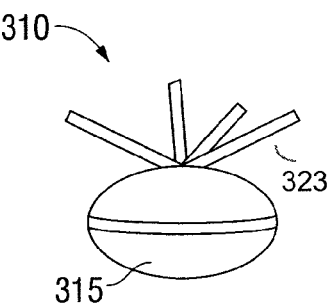
FIG. 4A     FIG. 4B     FIG. 4C
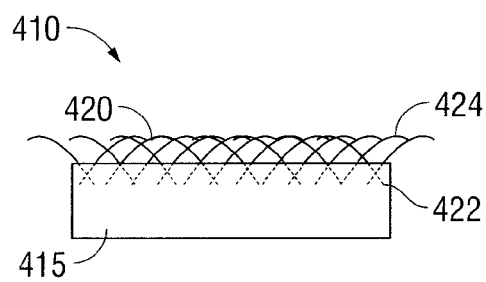
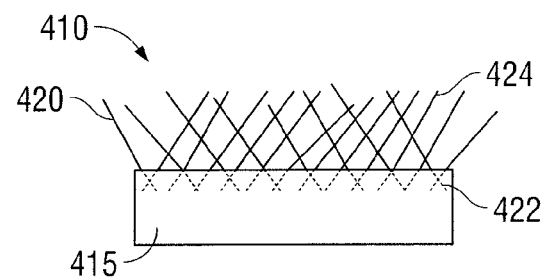
FIG. 5A     FIG. 5B
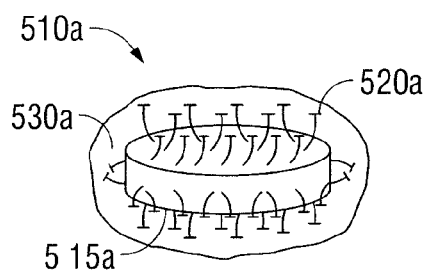
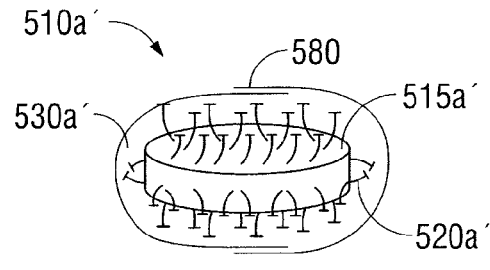
FIG. 6A     FIG. 6B

ORAL DOSAGE FORMS FOR DELIVERY OF THERAPEUTIC AGENTS

CROSS-REFERENCE TO RELATED APPLICATION

The present application claims the benefit of and priority to U.S. Provisional Application Ser. No. 61/262,963, filed on Nov. 20, 2009, the entire disclosure of which is incorporated herein by reference.

BACKGROUND

1. Technical Field

The present disclosure relates generally to the delivery of therapeutic agents, and more particularly, to oral dosage forms for the delivery of therapeutic agents which include an inner core, a therapeutic agent and a mechanical fastener for engaging tissue of the gastrointestinal tract.

2. Background of Related Art

The self-administration of oral dosage forms may often be fraught with non-compliance problems. While some patients may not like the taste or feel of certain dosage forms, others may simply forget to take the orally-administered therapeutic agents at the appropriate times.

Studies suggest that about one-half of the patients for whom appropriate medication is prescribed fail to receive the full benefits because of inadequate adherence to treatment. The consequences of poor adherence to long-term therapies may include compromised treatments, poor health outcomes and increased health care costs.

It would be beneficial to provide an oral dosage form which may replace the conventional self-administration of orally administered medications. Oral dosage forms which require less frequent self-administration may improve compliance thereby improving treatment options and health outcomes while decreasing health care costs.

SUMMARY

Oral dosage forms in accordance with the present disclosure may sustain delivery of a therapeutic agent by engaging the tissue of the gastrointestinal tract and prolonging the activity of the oral dosage form in the gastrointestinal tract. The oral dosage forms include at least one inner core and at least one mechanical fastener. The inner core includes at least one therapeutic agent. The mechanical fastener, which is positioned on at least a portion of the inner core, provides the dosage form with the ability to engage the tissue of the gastrointestinal tract.

In embodiments, the mechanical fasteners may be positioned on at least a portion of the inner core, wherein the mechanical fastener is capable of transitioning between a first non-gripping position and a second tissue-gripping position.

In certain embodiments, the oral dosage forms further include an outer protective layer which covers at least a portion of the mechanical fasteners. In embodiments, the outer protective layer may completely encases the mechanical fasteners. In other embodiments, the outer protective layer completely encases the inner core.

In other embodiments, the oral dosage form includes a plurality of inner cores, each inner core containing a therapeutic agent. The dosage forms in accordance with these embodiments include a plurality of mechanical fasteners positioned on at least a portion of each of the plurality of inner cores, and at least one outer protective layer encasing the mechanical fasteners.

In still other embodiments, in accordance with the present disclosure oral dosage forms include a plurality of inner cores containing a therapeutic agent and each having a plurality of mechanical fasteners, and a first outer protective layer encasing at least one of the mechanical fasteners on at least one of the plurality of inner cores. Dosage forms in accordance with these embodiments further include a second outer protective layer which encases the first protective outer layer and at least one of the plurality of inner cores.

Methods for delivering therapeutic agents are also disclosed.

BRIEF DESCRIPTION OF THE DRAWINGS

Various embodiments of the present disclosure will be discussed in more detail below in conjunction with selected embodiments and the appended drawings wherein:

FIGS. 4A and 4C show perspective views of yet another embodiment of an oral dosage form according to the present disclosure;

FIG. 4B shows a cross-sectional view of the oral dosage form shown in FIG. 4A;

FIGS. 5A and 5B show a side view of yet another embodiment of an oral dosage form according to the present disclosure;

FIG. 6A shows a perspective view of one embodiment wherein the oral dosage form is a tablet according to the present disclosure;

FIG. 6B shows a side view of one embodiment wherein the oral dosage form is a capsule according to the present disclosure;

DETAILED DESCRIPTION

Figure 1:
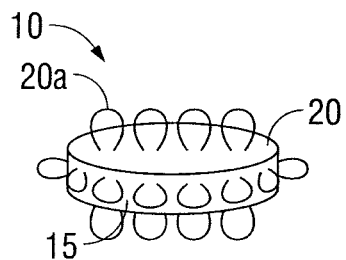
FIG. 1 shows a perspective view of one embodiment of an oral dosage form according to the present disclosure.

Oral dosage forms in accordance with the present disclosure include an inner core and at least one mechanical fastener for engaging tissue along the gastrointestinal tract. The inner core includes at least one therapeutic agent. The at least one mechanical fastener is positioned on a portion of the inner core. In embodiments, the oral dosage form may further include an outer protective layer which encases the at least one mechanical fastener. In still other embodiments, the oral dosage forms may include more than one outer protective layer.

In some embodiments, the oral dosage forms described herein may be designed to degrade along any portion of the gastrointestinal tract, including the mouth, esophagus, stomach, duodenum, jejunum, ileum, large intestine, sigmoid colon, rectum, and anus. The term degrade refers to the breakdown of the oral dosage form inside the gastrointestinal tract and is intended to include other similar terms, such as dissolve, erode, absorb, disintegrate and the like. In other embodiments discussed herein, oral dosage forms may release therapeutic agents, subsequently separate from the gastrointestinal tract, and are excreted from the body via natural passageways.

The oral dosage forms described herein may degrade from the outer surface of the dosage form inward towards the center of the inner core. However, in embodiments, the present oral dosage forms provide sustained release formulations, such as osmotic pumps, and the oral dosage forms may include a tiny hole which allows for the oral dosage form to slowly degrade over time from the inside out, thereby passing the therapeutic agent from inside the inner core outwardly through the hole.

The oral dosage forms include an inner core which may control the onset and release characteristics of the therapeutic agent. The inner core may deliver a therapeutic agent by immediate release, a delayed release, a sustained release or any combination of release profiles.

"Immediate" and "delayed" release refers to the onset of release in relationship to administration of the therapeutic agent. "Immediate" refers to the release of a therapeutic agent which begins within a relatively short time after administration, e.g., a few minutes or less. "Delayed" refers to the release of therapeutic agent which may be postponed, and may begin or be triggered some period of time after administration (e.g., a lag time), typically a relatively long period of time, e.g., more than one hour.

"Sustained" refers to the period of on-going release, and means that the delivery of therapeutic agent goes on (it continues or is sustained) for an extended period of time after initial onset, typically more than one hour, whatever the shape of the dose release profile. For example, the release of the therapeutic agent may be sustained between a maximum and minimum value (more than zero) for some relatively long period of time, i.e., a week, a month, a year. This release may be at a constant dose, or at a dose which diminishes or tapers off over time.

The inner core may be a core-seed or matrix. The core-seed can be sugar spheres, spheres made from microcrystalline cellulose, and any suitable drug crystals. An exemplary inner core may include a sugar core. Exemplary matrices include hydrophilic matrixes. Some non-limiting examples of materials useful for forming a hydrophilic matrix include hydroxypropyl methylcellulose (HPMC), hydroxypropyl cellulose (HPC), poly(ethylene oxide), poly (vinyl alcohol), xanthan gum, carbomer, carrageenan, and zooglan. Other similar hydrophilic polymers may also be employed.

In some embodiments, the inner core may include materials which allow for the immediate release of the therapeutic agent. Immediate release of the therapeutic agent may occur from the inner core using any of variety of methods known in to those skilled in the art. For example, the inner core may include a very thin layer, or a highly water soluble material, or coating of material which by virtue of its thinness is quickly penetrated by gastric fluid allowing rapid leaching of the therapeutic agent. Another example may be by incorporating the therapeutic agent in a mixture that includes a supporting binder or other inert material that dissolves readily in gastric fluid, releasing the therapeutic agent as the material dissolves. A third may include the use of a supporting binder or other inert material that rapidly disintegrates upon contact with gastric fluid, with both the material and the therapeutic agent quickly dispersing into the fluid as small particles. Examples of materials that rapidly disintegrate and disperse are lactose and microcrystalline cellulose. An example of a suspending agent and binder is hydroxypropyl methylcellulose.

In other embodiments, the inner core may include materials suitable for delaying the release of the therapeutic agent, such as materials used in forming enteric matrices and/or coatings. Enteric matrices or coatings for the delayed release of the therapeutic agent may be pH-dependent or pH-independent. In embodiments, enteric coatings may protect the inner core in the stomach, while breaking down in the large or small intestine for exposure or absorption of the inner core and therapeutic agent. Enteric matrices or coatings which are pH dependent may be activated to release the therapeutic agent within a known pH range, which typically is matched to the local pH of the environment where delayed release is desired. Exemplary pH dependent coatings may include materials such as cellulose acetate phthalate, cellulose acetate trimellitate, hydroxypropyl methylcellulose phthalate, polyvinyl acetate phthalate, sodium alginate, carboxymethylethylcellulose, co-polymerized methacrylic acid/methacrylic acid methyl esters. Some of these materials may also be known under the trade name EUDRAGIT® L12.5, L100, or EUDRAGIT® S12.5, S100 or similar compounds used to obtain enteric coatings. Aqueous colloidal polymer dispersions or re-dispersions may also be applied, e.g., EUDRAGIT® L 30D-55, EUDRAGIT® L100-55, EUDRAGIT® S100, EUDRAGIT® preparation 4110D (Rohm Pharma); AQUATERIC®, AQUACOAT® CPD 30 (FMC); KOLLICOAT MAE® 30D and 30DP (BASF); EASTACRYL® 30D (Eastman Chemical).

A pH independent coating or matrix includes materials which are not activated to release the therapeutic agent within a known pH range. In some embodiments, a pH independent coating includes materials which may be susceptible to enzymatic activation by azo-reductases in intestinal bacteria (e.g., azo-polymers) or materials susceptible to degradation by polysaccharidases in the colon (e.g., natural polysaccharides). Non-limiting examples of azo-polymers include co-polymers of 2-hydroxyethyl methacrylate (HEMA) and methyl methacrylate (MMA). Non-limiting examples of natural polysaccharides include amylose, chitosan, chrondoitin, dextran, and xylan.

In still other embodiments, the inner core may include materials suitable for sustained release of the therapeutic agent. Some examples of suitable materials include, but are not meant to be limited to, sustained release coatings, sustained release matrices, and sustained release osmotic systems. Sustained release coatings can be prepared using a water-insoluble polymer, a combination of water-insoluble polymers, or a combination of water-insoluble and water-soluble polymers. Conventional sustained release polymers well known to those of ordinary skill in the formulary arts can be used for the sustained release matrix.

Exemplary sustained release matrices and/or coatings can include polyvinyl acetate, cellulose acetate, cellulose acetate butyrate, cellulose acetate propionate, ethyl cellulose, fatty acids and esters thereof, alkyl alcohols, waxes, ceresin, casein, paraffin, gelatin-formaldehyde, keratin, glueten, zein (prolamine from corn), and aqueous polymeric dispersions such as EUDRAGIT® RS and RL30D, EUDRAGIT® NE30D, AQUACOAT®, SURELEASE®, KOLLICOAT® SR30D, and cellulose acetate latex.

The term oral dosage form refers to the physical form of at least one therapeutic agent intended for administration or consumption via the mouth. Some common non-limiting examples of oral dosage forms include pills, tablets, capsules, wafers, pellets, or caplets. Each of the oral dosage forms described herein include at least one inner core containing at least one therapeutic agent and at least one mechanical fastener positioned on a portion of the inner core.

In embodiments, the oral dosage forms may include a plurality of inner cores. In such embodiments, each inner core may include at least one therapeutic agent. In some embodiments, each inner core may include different therapeutic agents. In still other embodiments, each inner core may include the same therapeutic agent. The therapeutic agent may be used in equal or different amounts in each inner core.

The term "therapeutic agent", as used herein, is used in its broadest sense and includes any substance or mixture of substances that provide clinical use. A therapeutic agent could be any agent which provides a therapeutic or prophylactic effect, a compound that affects or participates in tissue growth, cell growth, cell differentiation, a compound that may be able to invoke a biological action such as an immune response, or could play any other role in one or more biological processes.

Examples of therapeutic agents which may be utilized in accordance with the present disclosure include drugs, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; cells, viruses, and ribozymes.

In embodiments, the therapeutic agent may include at least one of the following drugs, including combinations and alternative forms of the drugs such as alternative salt forms, free acid form, free base forms, pro-drugs and hydrates: analgesics/antipyretics (e.g., aspirin, gabapentin, pregabalin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, capsaicin, and meprobamate); antiasthmatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconazole, amphotericin B, nystatin, and candicidin); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone); antineoplastics (e.g., cyclophosphamide, actinomycin, bleomycin, dactinomycin, daunorubicin, doxorubicin, epirubicin, mitomycin, methotrexate, fluorouracil, gemcitabine, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, goserelin, leuprolide, tamoxifen, interferon alfa, retinoic acid (ATRA), nitrogen mustard alkylating agents, and piposulfan); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propanolol, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encamide, digoxin, digitoxin, mexiletine, disopyramide phosphate, procainamide, quinidine sulfate, quinidine gluconate, quinidine polygalacturonate, flecamide acetate, tocamide, and lidocaine); antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenyloin, phenyloin sodium, clonazepam, primidone, phenobarbitol, carbamazepine, amobarbital sodium, methsuximide, metharbital, mephobarbital, mephenyloin, phensuximide, paramethadione, ethotoin, phenacemide, secobarbital sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and); agents useful for calcium regulation (e.g., calcitonin, and parathyroid hormone); antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime e axetil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone propionate; steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium); hypoglycemic agents (e.g., human insulin, purified beef insulin, purified pork insulin, glyburide, chlorpropamide, glipizide, tolbutamide, and tolazamide); hypolipidemic agents (e.g., clofibrate, dextrothyroxine sodium, probucol, pravastitin, atorvastatin, lovastatin, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); as well as other drugs useful in the compositions and methods described herein include mitotane, halonitrosoureas, anthrocyclines, ellipticine, ceftriaxone, ketoconazole, ceftazidime, oxaprozin, albuterol, valacyclovir, urofollitropin, famciclovir, flutamide, enalapril, metformin, itraconazole, buspirone, gabapentin, fosinopril, tramadol, acarbose, lorazepam, follitropin, glipizide, omeprazole, fluoxetine, lisinopril, tramadol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecamide, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. In some embodiments, the drug may be water soluble. In some embodiments, the drug may not be water soluble. Alternatively, some embodiments of the present disclosure may be used to administer vitamins and/or minerals.

Various forms of the drugs and/or other therapeutic agents may be used. These include, without limitation, such forms as uncharged molecules, molecular complexes, salts, ethers, esters, amides, and the like, which may be biologically activated following oral administration or otherwise inserted into the gastrointestinal tract.

The therapeutic agents may be used in amounts that are therapeutically effective, which varies widely depending largely on the particular therapeutic agent being used. The amount of therapeutic agent incorporated into the composition also depends upon the desired release profile, the concentration of the agent required for a biological effect, and the length of time that the therapeutic agent should be released for treatment.

The upper and lower limits of the amount of therapeutic agent incorporated into the oral dosage forms may be dependent upon the activity of the therapeutic agent and the length of time needed for treatment. Thus, the amount of the therapeutic agent should not be so small that it fails to produce the desired physiological effect, nor so large that the therapeutic agent is released in an uncontrollable or potentially harmful manner.

Typically, within these limits, amounts of the therapeutic agents from about 0.1% up to about 95%, and preferably from about 1% to about 70% by weight, can be incorporated into the present compositions. However, lesser amounts may be used to achieve efficacious levels of treatment for therapeutic agents that are particularly potent.

Dosage forms in accordance with the present disclosure further include at least one mechanical fastener which in certain embodiments, protrude from a surface of the inner core. The mechanical fastener may be made from at least one filament. The mechanical fastener may protrude from the surface of the inner core in a generally perpendicular direction. In embodiments, a plurality of mechanical fasteners may be positioned over an entire surface of the inner core. In other embodiments, a plurality of mechanical fasteners may be positioned over only a portion of the surface of the inner core. In still other embodiments, the mechanical fasteners may protrude from more than one surface of the inner core.

The mechanical fastener may take the configuration of any shape, size or dimension, suitable for engaging the tissue in the gastrointestinal tract of a mammal. For example, the mechanical fastener may simply be straight spikes which extend a sufficient length from the surface of the inner core to engage the gastrointestinal tissue without disrupting the inner cores ability to release the therapeutic agent contained therein.

In some embodiments, the mechanical fastener may represent a generally hook-shaped configuration wherein a proximal portion of the fastener is straight and a distal portion of the fastener is curled or includes a rounded edge. In other embodiments, the mechanical fastener may include a proximal portion of the fastener which is straight and a distal portion of the fastener which may include naps. Naps refer to ends of the fastener which have been modified to increase the fasteners ability to grip tissue. For example, the ends of the fasteners may be heated to melt the distal portion of the fastener to increase the surface area of the distal end of the fastener. In another example, the ends of the fastener may be cut, or ground to create a jagged edge which provides the distal end of the fastener with an increased surface area useful for engaging tissue. In certain embodiments, the mechanical fastener may include at least one barb, surface protrusion, an undulated surface, or mechanically roughened surface, increasing the surface area of the oral dosage form. By engaging tissue, the oral dosage forms maintain the ability to either permanently fixate onto a single section of the gastrointestinal tract and/or to temporarily and intermittently attach to or get caught on different portions of gastrointestinal tissue while being passed through the gastrointestinal tract.

The mechanical fastener described herein may be made from any biocompatible material. Thus, the fasteners may be formed from a natural material or a synthetic material. The material from which the fasteners are formed may be bioabsorbable or non-bioabsorbable. It should of course be understood that any combination of natural, synthetic, bioabsorbable and non-bioabsorbable materials may be used to faun the fasteners. Some non-limiting examples of materials from which the fasteners may be made include, but are not limited to poly(lactic acid), poly (glycolic acid), poly(trimethylene carbonate), poly (dioxanone), poly (hydroxybutyrate), poly (phosphazine), polyesters, polyethylene terephthalate, ultra-high molecular weight polyethylene, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly (amino acids), copoly (ether-esters), polyalkylene oxalates, poly (saccharides), polyamides, poly (iminocarbonates), polyalkylene oxalates, polyoxaesters, polyorthoesters, polyphosphazenes, polyurethanes, biopolymers, polymer drugs and copolymers, block copolymers, homopolymers, blends and combinations thereof.

The mechanical fastener(s) may also be made of any suitable shape memory material. Suitable shape memory materials include shape memory polymers and shape memory alloys. A variety of shape memory polymers and shape memory alloys, which may be formed into filaments useful as the mechanical fastener of the present oral dosage form, are known to those skilled in the art.

Suitable shape memory alloys (capable of being spun into filaments) that can be used to form the mechanical fasteners include, but are not limited to, nitinol (NiTi), CuZnAl, CuAlNi, CuNiTi and FeNiAl. Methods for forming fibers from shape memory alloys are within the purview of those skilled in the art.

Shape memory polymers are those that may be conditioned using two separate phases or three separate phases. Two-phase shape memory polymers may be polymers which have both a current form (temporary) and a stored form (permanent). Once the latter has been manufactured by any conventional method, the polymer may be changed into a temporary form by processing the polymer through heating, deformation, and cooling. After cooling, the polymer maintains the temporary shape until the polymer is activated by a predetermined external stimulus. In addition to temperature change, the shape memory polymers can also conditioned and/or activated by electric or magnetic fields, light, and/or a change in pH. Upon activation, the polymer shape transitions back to the permanent shape. Suitable shape memory polymers include those listed below.

In some embodiments, the mechanical fasteners may consist of polymeric monofilaments manufactured in a straight state. That is to say the permanent shape of the shape memory monofilaments is generally straight. The straight polymeric monofilaments may be heated above the polymer's glass transition temperature (Tg), which allows the polymer to become soft, flexible, and easier to shape. While above the Tg, the straight polymeric monofilaments may be curled. The curled polymeric monofilaments may then be cooled below the Tg of the polymer to keep the monofilaments in the curled, temporary shape. In such embodiments, the curled polymeric monofilaments may be conditioned to return to the permanent form, i.e., straightened, upon exposure to the proper external stimulus, such as a change in temperature above the Tg of the given polymer.

Although specifically recited as a polymeric monofilament, it is envisioned that the mechanical fasteners may also be formed from a plurality of monofilaments, mutli-filaments, yarns and braids formed by a plurality of multifilaments and staple fibers. In addition, the shape memory polymers may be combined with any variety of biocompatible materials to form the mechanical fasteners.

It is envisioned that the polymeric mechanical fasteners may be conditioned as shape memory polymers in the presence of or the absence of the inner core. In embodiments, the mechanical fasteners may be conditioned prior to being incorporated into the inner core. In other embodiments, the mechanical fasteners may be conditioned after being incorporated into the inner core. In still other embodiments, the mechanical fasteners may be attached to the inner core by any suitable method, including, but not limited to adhesives.

In some embodiments, the shape memory polymer used to form the mechanical fasteners may display a Tg ranging from about 20° C. to about 40° C. In such embodiments, the mechanical fasteners will transition from the temporary shape to the permanent shape when exposed to temperatures in this range. In specific embodiments, the shape memory polymer will be programmed to transition at body temperature, which is about 37° C.

In other embodiments, the shape memory polymers may include at least one hard segment and at least one soft segment or multiple soft segments that are covalently crosslinked, wherein at least two of the segments are linked via a functional group which is cleavable under application of light, changes in ionic concentration, changes in pH, electric field, magnetic field, and/or ultrasound. In addition to changing shape in response to changes in temperature, the compositions can change shape in response to application of light, changes in ionic concentration, changes in pH, electric field, magnetic field and/or ultrasound. The temporary shape in these polymers is fixed by the covalent crosslinks.

Various functional groups are known to crosslink in the presence of certain ions or in response to changes in pH. For example, calcium ions are known to crosslink amine and alcohol groups, i.e., the amine groups on alginate can be crosslinked with calcium ions. Also, carboxylate and amine groups become charged species at certain pHs. When these species are charged, they can crosslink with ions of the opposite charge. The presence of functional groups which respond to changes in the concentration of an ionic species and/or to changes in pH on hard and/or soft segments results in reversible linkages between these segments. One can fix the temporary shape of the mechanical fastener while crosslinking the segments. After the shape has been deformed, alteration of the ionic concentration or pH can result in cleavage of the ionic interactions which formed the crosslinks between the segments, thereby relieving the strain caused by the deformation and thus returning the mechanical fastener to its permanent straightened shape. Because ionic bonds are made and broken in this process, it can only be per-formed once. The bonds, however, can be re-formed by altering the ionic concentration and/or pH, so the process can be repeated as desired.

Different portions of the gastrointestinal tract maintain different pH levels, thus the mechanical fasteners may be made of shape memory polymers which are pH sensitive and may be designed to change shape when exposed to a pH of the certain portion of the gastrointestinal tract. For example, the mechanical fastener may be made from shape memory materials that are activated at a pH ranging from about 6.0 to about 6.5, i.e., the pH of the duodenum. Such fasteners will not be activated while passing through the stomach, which displays a pH of about 1 to about 3. More specifically, mechanical fasteners may be manufactured utilizing methods and materials which enable the fasteners to protrude from the inner core, allowing the oral dosage form to fixate in the large intestine in response to recognizing a change in acidity (pH) from the stomach to the large intestine.

In another example, the mechanical fastener may be made from shape memory materials that are activated at a pH ranging from about 7 to about 8, i.e., the pH of the small intestine. Such fasteners will not be activated while passing through the esophagus, which displays a pH of about 5 to about 6.

Suitable shape memory polymeric materials which may be utilized to fashion the mechanical fasteners include: polyurethanes; poly(styrene-butadiene) block copolymers; polynorbornenes; caprolactones; dioxanones; diol esters including oligo (epsilon caprolactone) diol; lactic acid; glycolic acid; ether-ester diols including oligo (p-dioxanone) diol; carbonates including trimethylene carbonate; combinations thereof; and the like. In embodiments, the shape memory polymer may be a copolymer of two components with different thermal characteristics, including: oligo (epsilon-caprolactone) dimethacrylates and butyl acrylates including poly(epsilon-caprolactone) dimethacrylate-poly (n-butyl acrylate); or a diol ester and an ether-ester diol such as oligo (epsilon caprolactone) diol/oligo (p-dioxanone) diol copolymers. These multi-block oligo (epsilon-caprolactone) diol/oligo (p-dioxanone) diol copolymers possess two block segments: a "hard" segment and a "switching" segment linked together in linear chains. Such materials are disclosed, for example, in Lendlein, "Shape Memory Polymers-Biodegradable Sutures," Materials World, Vol. 10, no. 7, pp. 29-30 (July 2002), the entire disclosure of which is incorporated by reference herein.

In other embodiments, blends of materials may be utilized as the shape memory polymeric material including: urethanes blended with lactic acid and/or glycolic acid; homopolymers thereof or copolymers thereof; and acrylates blended with caprolactones such as polycaprolactone dimethacrylate poly(butyl acrylate) blends; and combinations thereof.

Other examples of these shape memory polymers and methods for forming permanent and temporary shapes therewith are set forth in Lendlein et al., "Shape memory polymers as stimuli-sensitive implant materials," Clinical Hemorheology and Microcirculation, 32 (2005) 105-116, and Lendlein et al., "Biodegradable, Elastic Shape-Memory Polymers for Potential Biomedical Applications," Science, Vol. 269 (2002) 1673-1676, the entire disclosures of each of which are incorporated by reference herein.

In addition to shape memory polymers which react to changes in temperature and pH, some additionally useful shape memory polymers include those which react to a change in ionicity, charge, electric and/or magnetic conditions.

In some embodiments, the mechanical fasteners may possess a first, generally curled configuration at a temperature less than about 20° C. and may assume a second, generally straight configuration when exposed to a temperature ranging from about 20° C. to about 40° C. In other embodiments, the mechanical fasteners may possess a first, generally curled configuration at a pH greater than about 7 and may assume a second, generally straight configuration when exposed to a pH ranging from about 1 to about 6.9.

Although the mechanical fasteners are disclosed predominantly as transitioning from curled to straight, it is well within the scope of the present disclosure to include mechanical fasteners that may transition to any number of different shapes and dimensions. For example, mechanical fasteners may also transition from a generally flat position, adjacent a surface of the inner core, to a second, outwardly protruding configuration. The two different configurations between which the mechanical fasteners can transition may be determined at the time of conditioning the shape memory polymer. In embodiments, the mechanical fasteners may assume any shape suitable for delivery via the mouth and passing through the gastrointestinal tract. In the most general sense, upon exposure to a stimulus, the mechanical fasteners transition between two different configurations, a first, non-gripping configuration and a second, gripping configuration.

In additional to the inner core and the mechanical fasteners, the oral dosage forms described herein may also include at least one outer protective layer. The mechanical fasteners may be encased by at least one protective layer. A protective layer may be added to a portion of the mechanical fasteners to prevent the fasteners from prematurely engaging tissue in the gastrointestinal tract. The protective layer may be made from a material which degrades over time, or in certain environmental conditions, to expose the mechanical fasteners. The protective layer may control the point in time at which the mechanical fasteners become exposed and are capable of engaging the tissue. The amount of time it takes for the protective layer to degrade inside the gastrointestinal tract may vary according to the materials used.

In embodiments, the outer protective layer may include materials suitable for immediate exposure of the mechanical fasteners. These materials may dissolve away quickly upon exposure to saliva, mucous, bile or other bodily fluids found within the gastrointestinal tract, thereby allowing the mechanical fasteners to engage tissue rather quickly within the mouth, esophagus or stomach.

In other embodiments, the protective layer may include materials suitable for delaying the exposure of the mechanical fasteners, such as materials used in forming enteric matrixes and/or coatings. Enteric matrixes or coatings for the delayed exposure of the mechanical fasteners may be pH-dependent or pH-independent. Enteric matrixes or coatings which may be pH dependent may expose the mechanical fasteners within a known pH range, which typically is matched to the local pH of the environment where delayed exposure is desired. Exemplary pH dependent coatings may include materials such as cellulose acetate phthalate, cellulose acetate trimellitate, hydroxypropyl methylcellulose phthalate, polyvinyl acetate phthalate, carboxymethylethylcellulose, co-polymerized methacrylic acid/methacrylic acid methyl esters. Some of these materials may also be known under the trade name EUDRAGIT® L12.5, L100, or EUDRAGIT® S12.5, S100 or similar compounds used to obtain enteric coatings. Aqueous colloidal polymer dispersions or re-dispersions may also be applied, e.g. EUDRAGIT® L 30D-55, EUDRAGIT® L100-55, EUDRAGIT® S100, EUDRAGIT® preparation 4110D (Rohm Pharma); AQUATERIC®, AQUACOAT® CPD 30 (FMC); KOLLICOAT MAE® 30D and 30DP (BASF); EASTACRYL® 30D (Eastman Chemical).

A pH independent coating or matrix includes materials which do not require a certain pH to exposure the mechanical fasteners. In some embodiments, a pH independent coating includes materials which may be susceptible to enzymatic activation by azo-reductases in intestinal bacteria (i.e., azo-polymers) or materials susceptible to degradation by polysaccharidases in the colon (natural polysaccharides). Non-limiting examples of azo-polymers include co-polymers of 2-hydroxyethyl methacrylate (HEMA) and methyl methacrylate (MMA). Non-limiting examples of natural polysaccharides include amylose, chitosan, chrondoitin, dextran, and xylan.

In still other embodiments, the outer protective layers may include, but are not limited to, materials such as hydroxypropyl methylcellulose (HPMC), hydroxypropyl cellulose (HPC), poly(ethylene oxide), poly(vinyl alcohol), xanthan gum, carbomer, carrageenan, zooglan, polyvinyl acetate, cellulose acetate, cellulose acetate butyrate, cellulose acetate propionate, ethyl cellulose, fatty acids and esters thereof, alkyl alcohols, waxes, zein (prolamine from corn), and aqueous polymeric dispersions such as EUDRAGIT® RS and RL30D, EUDRAGIT® NE30D, AQUACOAT®, SURELEASE®, KOLLICOAT® SR30D, and cellulose acetate latex.

A therapeutic agent may also been incorporated into the outer protective layer. Release of the therapeutic agent from the outer protective layer may be immediate, delayed or sustained over a lengthy period of time.

In some embodiments, a therapeutic agent may be positioned on an outer surface of the protective layer to provide a bolus dose of the agent prior to the degradation of the inner core and/or the outer protective layer. The therapeutic agent may be positioned along any portion of the outer surface of the outer protective layer.

It is envisioned that the outer protective layer may be applied to the mechanical fasteners in the presence or absence of the inner core. For example, the mechanical fasteners may be encased within the outer protective layer prior to being incorporated into the inner core. In some embodiments, the mechanical fasteners may be encased by the outer protective layer after being incorporated into the inner core. In other embodiments, the mechanical fasteners may be attached to the inner core by the assistance of the outer protective layer. In still other embodiments, at least a portion of the inner core may be compressed or molded around the mechanical fastener prior the addition of the protective layer.

In some embodiments, the oral dosage forms may include a plurality of inner cores having a plurality of mechanical fasteners. In such embodiments, each inner core/mechanical fastener combination may include a separate protective layer. In some embodiments, each inner core/mechanical fastener combination may include protective layers made of different materials. In still other embodiments, each inner core/mechanical fastener combination may include protective layers made of the same materials. In yet other embodiments, plurality of inner cores and mechanical fasteners may be encased within a single outer protective layer.

In addition to the therapeutic agent, the oral dosage forms described herein may include any variety or combination of suitable excipients commonly used in forming oral dosage forms, such as pellets, pills, tablets, capsules, caplets and the like. Some non-limiting examples of useful excipients include plasticizers, lubricants, binding agents, disintegration agents, filling agents, glidants, colorants, fragrances, taste-modifiers, sweeteners, surfactants, stabilizers, and combinations thereof. The excipients, like the therapeutic agents, may be combined with any portion of the oral dosage forms previously described. For instance the excipients may be used in making the inner core, the outer protective layer, the mechanical fasteners and combinations thereof.

The excipients that can be employed in making the dosage forms are any of those commonly used in pharmaceutics and should be selected on the basis of compatibility with the therapeutic agent and the physicochemical properties of the inner core and/or outer protective layer. The excipients may represent up to 95% of the oral dosage form. In embodiments, the excipients may represent from about 1% to about 90% of the oral dosage form. Some more specific non-limiting examples of useful excipients are described below.

Binding agents may assist with holding the oral dosage form together. Some examples include, but are not limited to, cellulose derivatives such as methylcellulose, hydroxyethyl cellulose, hydroxypropyl cellulose, hydroxypropyl methylcellulose, polyvinylpyrrolidone, polyvinylpyrrolidone/vinyl acetate copolymer and the like.

Disintegrants ensure that the tablet breaks up in the digestive tract, and include materials such as corn starch, pregelatinized starch, cross-linked carboxymethylcellulose (AC-DI-SOL®), sodium starch glycolate (EXPLOTAB®), cross-linked polyvinylpyrrolidone (PLASDONE XL®), and any other disintegration agents used in tablet preparations.

Glidants and lubricants may be used to ensure efficient tableting during the manufacturing process, and some non-limiting examples include acetyltriethyl citrate, triethyl citrate, acetyltributyl citrate, dibutylsebacate, triacetin, polyethylene glycols, propylene glycol, talc, colloidal silica dioxide, silica gel, magnesium stearate, calcium stearate, titanium dioxide, magnesium silicate, leucine, glyceryl behenate, and the like.

Filling agents include, but are not limited to, materials such as lactose, calcium carbonate, calcium phosphate, calcium sulfate, microcrystalline cellulose, dextran, starches, sucrose, xylitol, lactitol, mannitol, sorbitol, sodium chloride, polyethylene glycol, and the like.

Surfactants may include sodium lauryl sulfate, sorbitan monooleate, polyoxyethylene sorbitan monooleate, bile salts, glyceryl monostearate, PLURONICS®, and the like.

Solubilizers may include citric acid, succinic acid, fumaric acid, malic acid, tartaric acid, maleic acid, glutaric acid sodium bicarbonate and sodium carbonate and the like. Stabilizers such as any antioxidants, buffers, acids, and the like, can also be utilized.

Flavors and sweeteners may be included to mask the taste of bad-tasting therapeutic agents; and pigments or colorants may be used to make the oral dosage foams visually attractive and/or easier to swallow.

The oral dosage forms described herein may be manufactured using any method or combinations of methods suitable for forming tablets, capsules, caplets, pellets, pills, and the like. For instance, the oral dosage form may be a tablet and may be formed by mixing the therapeutic agents with the material used to form the inner core, including any additional excipients, and pressing or compacting the mixture into a solid sufficient for swallowing. In some embodiments, a mechanical fastener may then be applied to a portion of the solid via an adhesive or additional film coating. In other embodiments, a mechanical fastener may combined with the mixture prior to pressing and the mixture may then be pressed in such a manner which allows at least a portion of the mechanical fastener to protrude from the surface of the pressed solid. In another example, the oral dosage forms may be a pill and may be formed by mixing the therapeutic agents with the material used to form the inner core, including any additional excipients, and rolling the mixture into a round solid shape suitable for orally delivery. Again, the mechanical fastener may be combined with the mixture or added after rolling.

In yet another example, the oral dosage forms may be a capsule which is intended to include singe-piece and multi-piece capsules, as well as hard-shelled and soft-shelled capsules. Most often, the capsule is a two-piece telescoping capsule which may be made from gelatin, starches, celluloses and the like. The two piece capsule includes two halves which are separated prior to filling. Like the tablet and the pill forms described above, a mixture of the therapeutic agents with the material used to form the inner core, including any additional excipients may be used to fill the capsule. The mechanical fasteners may be added to the mixture prior to being placed into the capsule. In other embodiments, the mechanical fasteners may be attached to the outside of the capsule.

In other embodiments, the ingredients of the oral dosage forms described herein may be processed. One example of a suitable process would include extrusion-spheronization, wherein the therapeutic agent, any excipients, and the material used to form the inner core may be granulated through the addition of a binder solution to form a wet mass. The wet mass may be passed through an extruder equipped with a certain size screen. The extrudates are spheronized in a marumerizer. The resulting pellets are dried, sieved and may be utilized in forming the oral dosage forms described herein.

Another suitable, non-limiting process, includes high-shear granulation wherein the therapeutic agent, any excipients, and the material used to form the inner core may be dry-mixed and then the mixture is wetted by addition of a binder solution in a high shear-granulator/mixer. The granules are kneaded after wetting by the combined actions of mixing and milling. The resulting granules or pellets are dried, sieved and may be utilized in forming the oral dosage forms described herein.

Yet another suitable process includes solution or suspension layering wherein the therapeutic agent and any excipients, may be put into a solution or dispersion with or without a binder and may be sprayed onto an inner core represented by core-seeds with a certain particle size in a fluid bed processor or other suitable equipment. The therapeutic agent may be coated on the surface of the starting seeds. The pellets loaded with the therapeutic agent may be dried and utilized in forming the oral dosage forms described herein.

An outer protective layer may be applied to the mechanical fastener either before or after being combined with the inner core. In some embodiments, the outer protective layer may encase the entire oral dosage form. In some embodiments, the outer protective layer may only cover a portion of the mechanical fastener.

In embodiments wherein the mechanical fastener may be made from a shape memory material, the mechanical fastener may be conditioned prior to or after being combined with the inner cores. In addition, the mechanical fastener may be able to transition between a first non-gripping position and a second, tissue-gripping position.

Turning now to FIG. 1, oral dosage form 10 includes inner core 15 which contains a therapeutic agent therein. Mechanical fasteners 20 are positioned on a least a portion of inner core 15. Mechanical fasteners 20 are shown as loops 20a which extend from the surface of inner core 15. Loops 20a may assist oral dosage form 10 with engaging gastrointestinal tissue.

Figure 2:
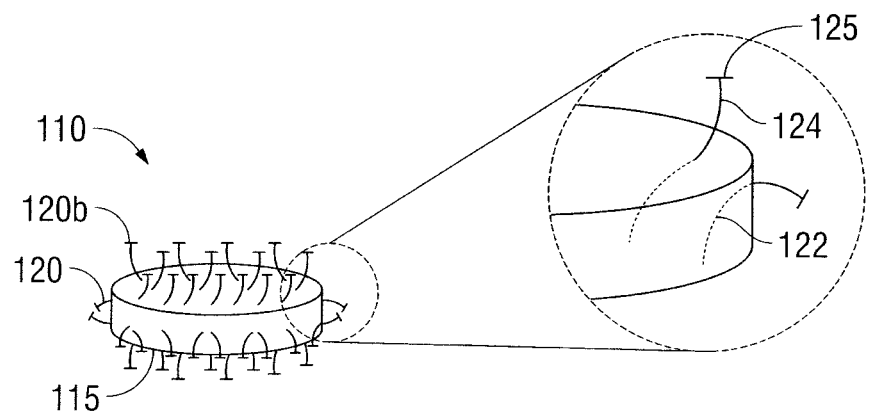
FIG. 2 shows a perspective view of another embodiment of an oral dosage form according to the present disclosure.

In some embodiments, the oral dosage form of FIG. 1 may be further processed to separate the loops into individual filaments. As illustrated in FIG. 2, oral dosage form 110 includes mechanical fasteners 120 which represent individual napped filaments 120b. In this embodiment, the individual filaments may have been formed by melting the top portions of loops 20a of FIG. 1 to create two separate filaments. Melting of a single loop may create two individual filaments 120b which each include a nap 125 at the distal end thereof.

Any suitable melting or thermosetting process may be used to separate the loops into two separate filaments. In addition, the loops may be separated using any suitable method including, but not limited to, cutting, grinding, lasering, and the use of ultra-sonics. In some embodiments, the loops may be processed individually. In other embodiments, more than one loop may be processed at a time.

In some embodiments, the oral dosage forms including loops (see FIG. 1) may be passed over a heated-cylinder to melt the distal most portion of the loop which comes in contact with the heated cylinder. In some instances, one or more rollers may be positioned near the heated cylinder to apply pressure on the oral dosage form in the direction of the heated cylinder. The roller(s) may be vertically displaced for controlling the pressing force on the oral dosage form. The temperature of the heated cylinder, the speed at which the oral dosage form is passed over the heated cylinder, and the amount of pressure optionally added to the oral dosage form may be controlled and or coordinated to make it possible to melt each loop into two individual napped filaments without damaging the oral dosage form.

Proximal portions 122 of napped filaments 120b are embedded in a portion of inner core 115 and distal portions 124 of napped filaments 120b extend from a surface of inner core 115 (FIG. 2). Naps 125 of napped filaments 120b increase the surface area of mechanical fasteners 120 thereby improving the ability of oral dosage form 110 to engage tissue within the gastrointestinal tract.

Figure 3:
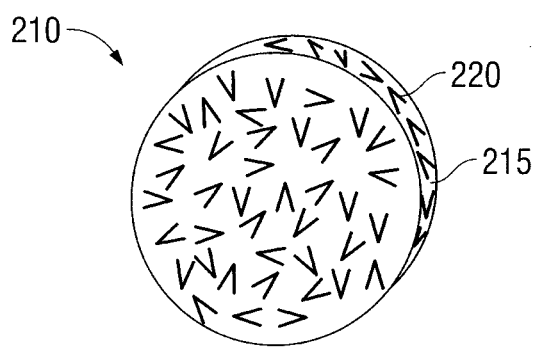
FIG. 3 shows a perspective view of still another embodiment of an oral dosage form according to the present disclosure.

In FIG. 3, oral dosage form 210 includes inner core 215 having mechanical fasteners 220 positioned thereon. Mechanical fasteners 220 represent generally V-shaped members which initially are covered by inner core 215. Following exposure to bodily fluids within the gastrointestinal tract, the outer surface 215a of inner core 215 will begin erode. Erosion of the outer surface of inner core 215 will expose mechanical fasteners 220 embedded beneath the outer surface. Mechanical fasteners 220 will eventually protrude from inner core 215 in alternating directions to provide oral dosage form 210 with an ability to engage tissue from many angles.

In FIGS. 4A-4C, oral dosage form 310 includes inner core 315 and mechanical fastener 320 made from a shape memory material. Mechanical fastener 320 includes a plurality of arms 323 extending from central post 322. As depicted in FIG. 4A, mechanical fastener 320 is in a first generally non-gripping position wherein arms 323 conform to the contour of the outer surface of inner core 315. By conforming to the contour of the outer surface of inner core 315, arms 323 provide a general smoothness to at least one surface of the dosage form thereby making the oral dosage form easier to swallow and provide a better feel to the patient prior to swallowing.

As shown in FIG. 4B, central post 322 is embedded in inner core 315 and passes through the center of inner core 315. Central post 322 is also attached to each of arms 323. Central post 322 anchors arms 323 to inner core 315 and maintains contact with inner core 315 as inner core 315 degrades over time.

In FIG. 4C, oral dosage form 310 is shown in a second tissue-gripping position. Mechanical fastener 320 may transition from a first generally non-gripping position to a second generally tissue-gripping position after being exposed to a certain stimulus or trigger, such as a certain pH level or body temperature. Arms 323 of mechanical fastener 320 extend upwardly and outwardly away from inner core 315 thereby allowing mechanical fastener 320 to engage tissue of the gastrointestinal tract. Release of the therapeutic agent may be controlled by the materials included in the inner core, or by other methods disclosed herein.

As illustrated in FIGS. 5A-5B, oral dosage form 410 includes inner core 415 and a plurality of mechanical fasteners 420 made from a shape memory material. Each mechanical fastener 420 includes proximal portion 422 which is embedded in a portion of inner core 415 and distal portion 424 which extends from a surface of inner core 415. As depicted in FIG. 5A, distal portion 424 of each mechanical fastener 420 is in a first, non-gripping position wherein distal portion 424 displays a substantially rounded configuration. A plurality of rounded mechanical fasteners 420 provide a general smoothness and overall rounded texture to at least one surface of oral dosage form 410 thereby making oral dosage form 410 easier to swallow.

In FIG. 5B, oral dosage form 410 is shown after being exposed to a certain stimulus or trigger, such as a certain pH level or body temperature. Distal portions 424 of mechanical fasteners 420 extend upwardly and outwardly away from inner core 415 thereby allowing mechanical fasteners 420 to engage tissue of the gastrointestinal tract.

In some embodiments, the oral dosage form includes an outer protective layer which encases the mechanical fastener. As shown in FIG. 6A, oral dosage form 510a is a tablet that includes inner core 515a which includes a therapeutic agent. Mechanical fasteners 520a are positioned around the outer perimeter of inner core 515a. Outer protective layer 530a entirely encases mechanical fasteners 520a prior to oral administration of dosage form.

Outer protective layer 530a is designed to dissolve or erode at the appropriate time in the gastrointestinal tract thereby exposing mechanical fasteners 520a. Oral dosage form 510a degrades from the outer surface of protective layer 530a inward towards the center of inner core 515a. Therefore, protective layer 530a will degrade first thereby exposing mechanical fasteners 520a. After exposure, mechanical fasteners 520a will engage tissue in the gastrointestinal tract and inner core 515a will begin to be exposed to the gastric fluids. Inner core 515a will degrade over time releasing the therapeutic agent into the gastrointestinal tract.

FIG. 6B is generally similar to FIG. 6A therefore all numerals and descriptions which are the same are designated with the prime mark and the differences will be described below. In FIG. 6B, oral dosage form 510a', i.e., a capsule, includes inner core 515a' which includes a therapeutic agent. Mechanical fasteners 520a' are positioned around the outer perimeter of inner core 515a'. Outer protective layer 530a' encases mechanical fasteners 520a'. Two-piece capsule 580 is positioned around the perimeter of protective layer 530a'.

Figure 7:
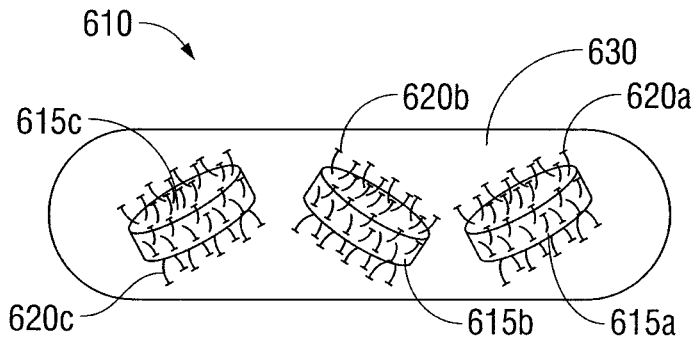
FIG. 7 shows a side view of another embodiment of an oral dosage form according to the present disclosure.

In the embodiments shown in FIG. 7, oral dosage form 610 includes a plurality of inner cores 615a-c. Each inner core includes mechanical fasteners 620a-c positioned on a surface thereof. Oral dosage form 610 further includes outer protective layer 630 which encases mechanical fasteners 620a-c and all three inner cores 615a-c, respectively. It is envisioned that following the erosion or degradation of outer protective layer 630, inner cores 615a-c will be released and free to circulate through the gastrointestinal tract. The plurality of inner cores 630a-c may engage the tissue of the gastrointestinal tract on an individual basis potentially treating a larger area of the gastrointestinal tract simultaneously.

Figure 8:
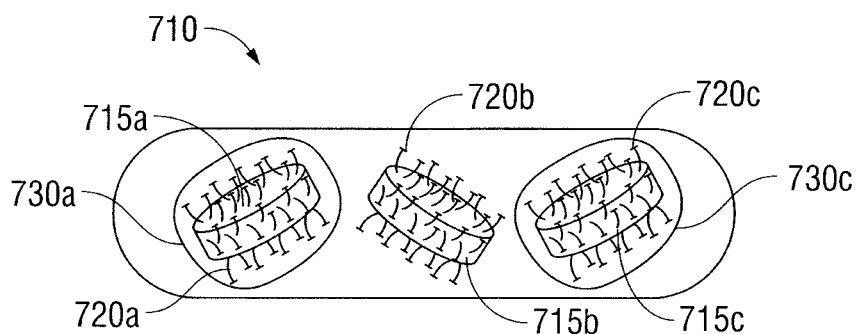
FIG. 8 shows a side view of yet another embodiment of an oral dosage form according to the present disclosure.

In FIG. 8, oral dosage form 710 again includes a plurality of inner cores 715a-c. Each inner core 715a-c includes a plurality of mechanical fasteners 720a-c. First outer protective layers 730a and 730c encase mechanical fasteners 720a and 720c, respectively. Second outer protective layer 740 encases mechanical fastener 720b, as well as first outer protective layers 730a and 730c. It is envisioned that upon degradation of the second outer protective layer, the plurality of inner cores may be released. The inner cores which include a first outer protective layer may be delayed from engaging gastrointestinal tissue and releasing the therapeutic agent. The inner core which does not include a first outer protective layer may immediately engage the gastrointestinal tissue upon release.

Figure 9:
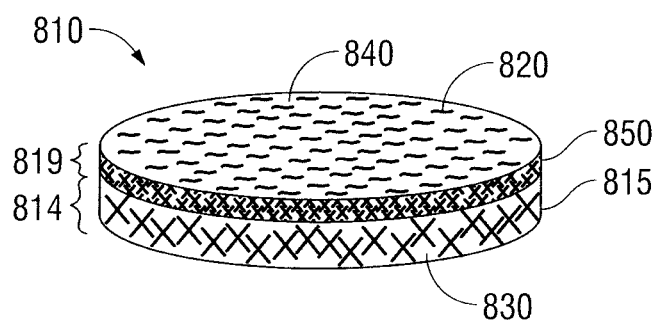
FIG. 9 shows a perspective view of still another embodiment of an oral dosage form according to the present disclosure.

In some embodiments, such as that shown in FIG. 9, oral dosage form 810 includes first portion 814 and second portion 819. First portion 814 includes inner core 815 coated with first outer protective layer 830. Second portion 819 includes mechanical fasteners 820 coated with second outer protective layer 840 for oral administration. Fasteners 820 are embedded in second outer protective layer 840. Degradation of second outer protective layer 840 exposes fasteners 820 on the surface of inner core 815. Adhesive 850 is positioned between first portion 814 and second portion 819 to form oral dosage 810. It is envisioned that the first and second outer protective layers may be made from the same or different materials.

Figure 10A:
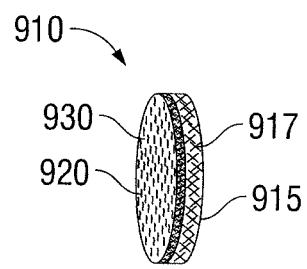
FIGS. 10A-10D show a sequence of mechanically fixating and delivering an oral therapeutic agent.
Figure 10B:
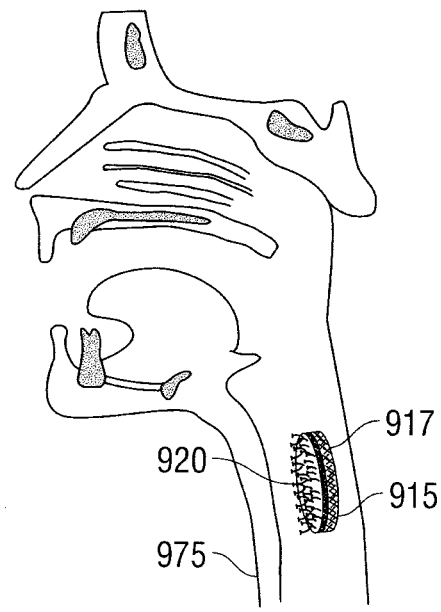
Figure 10C:
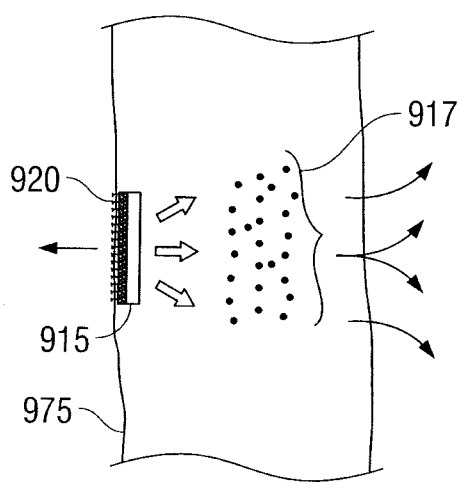
Figure 10D:
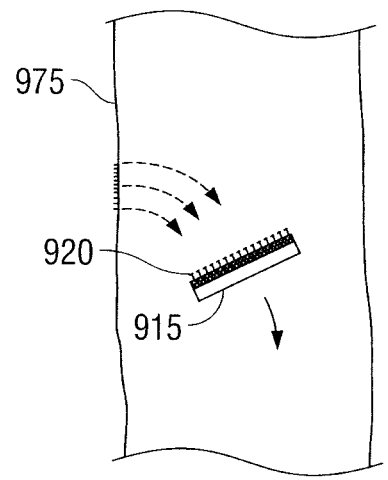

As illustrated in FIGS. 10A-10D, a sequence is shown wherein oral dosage form 910 is administered orally and allowed to engage the tissue 975 of the gastrointestinal tract to release therapeutic agent 917. Oral dosage form 910 includes inner core 915 containing therapeutic agent 917. Inner core 915 includes mechanical fasteners 920. At least a portion of mechanical fasteners are coated with protective layer 930. First, oral dosage form 910 is orally administered to a patient. In FIG. 10B, while passing through a portion of the gastrointestinal tract, protective layer 930 may be removed via degradation or erosion to expose mechanical fasteners 920. As shown in FIG. 10C, mechanical fasteners 920 may engage tissue 975 of the gastrointestinal tract thereby slowing the advancement of oral dosage form 910 through the gastrointestinal tract. As shown, mechanical fasteners 920 temporarily attach oral dosage form 910 to tissue 975 of the gastrointestinal tract. While engaging tissue 975, inner core 915 may begin to release therapeutic agent 917 into the gastrointestinal tract which may absorb the therapeutic agent. After a length of time, mechanical fasteners 920 may weaken via degradation by the body or by motility of the gastrointestinal tract. As depicted in FIG. 10D, oral dosage form 910 may become dislodged or unable to further engage the tissue of the gastrointestinal tract. Oral dosage form 910 may eventually be fully absorbed by the body or excreted via the colon.

The oral dosage forms described herein are suitable for delivering a therapeutic agent to a portion of a gastrointestinal tract of a mammalian patient. Any suitable method of oral delivery may be utilized. One such method includes administering an oral dosage fox in which includes an inner core containing at least one therapeutic agent, and having at least one mechanical fastener thereon for engaging tissue in the gastrointestinal tract with a protective layer encasing the at least one mechanical fastener. Following administration, interaction with bodily fluids will degrade the protective layer and expose the at least one mechanical fastener to a portion of the gastrointestinal tract. The mechanical fasteners then attach the oral dosage form to the tissue of the gastrointestinal tract, and degradation of the inner core will release the at least one therapeutic agent.

It will be understood that various modifications may be made to the embodiments disclosed herein. For example, any variety of inner core materials and outer protective layers may be used in forming the oral dosage forms described herein. As another example, the mechanical fasteners may also include at least one therapeutic agent. Thus, those skilled in the art will envision other modifications within the scope and spirit of the claims.

What is claimed is:

1. An oral dosage form comprising an inner core containing an outer surface and at least one therapeutic agent; and at least one filament extending from at least a portion of the outer surface of the inner core.

2. The oral dosage form of claim 1 wherein the inner core provides immediate release of the at least one therapeutic agent.

3. The oral dosage form of claim 1 wherein the inner core delays the release of the at least one therapeutic agent.

4. The oral dosage form of claim 1 wherein the inner core sustains the release of the at least one therapeutic agent.

5. The oral dosage form of claim 1 wherein a first portion of the at least one filament is embedded in the inner core and a second portion of the filament protrudes from the outer surface of the inner core.

6. The oral dosage form of claim 1 wherein the at least one filament is selected from the group consisting of loops, barbs, V-shaped filaments, hook-shaped filaments, napped filaments, straight filaments, and combinations thereof.

7. The oral dosage form of claim 1 wherein the at least one filament includes a first position and a second position.

8. The oral dosage form of claim 7 wherein the first position of the at least one filament is generally a non-gripping position.

9. The oral dosage form of claim 7 wherein the second position of the at least one filament is generally a tissue-gripping position.

10. The oral dosage form of claim 1 wherein the at least one filament is made from a shape memory material.

11. The oral dosage form of claim 10 wherein the shape memory material is selected from the group consisting of shape memory polymers, shape memory alloys and combinations thereof.

12. The oral dosage form of claim 1 wherein the dosage form is selected from the group consisting of pills, tablets, capsules, caplets, wafers, and pellets.

13. The oral dosage form of claim 1 further comprising an outer protective layer encasing the at least one filament.

14. The oral dosage form of claim 13 wherein the outer protective layer delays exposure of the at least one filament.

15. The oral dosage form of claim 12 wherein the outer protective layer further comprises at least one therapeutic agent.

16. The oral dosage form of claim 1 comprising: a plurality of inner cores, each inner core containing an outer surface and at least one therapeutic agent and having a plurality of filament extending from at least a portion of the outer surface of at least one of the plurality of inner cores; and a first outer protective layer encasing the plurality of filaments.

17. The oral dosage form of claim 16 comprising: a second outer protective layer encasing at least a portion of the plurality of filaments and at least a portion of the first outer protective layer.

18. A method of delivering a therapeutic agent to a portion of a gastrointestinal tract of a mammalian patient comprising: administering an oral dosage form which includes an inner core containing an outer surface and at least one therapeutic agent, and having at least one filament extending from at least a portion of the outer surface of the inner core for engaging tissue in the gastrointestinal tract with a protective layer encasing the at least one filament; exposing the at least one filament inside a portion of the gastrointestinal tract; attaching the oral dosage form to the tissue of the gastrointestinal tract, and releasing the at least one therapeutic agent.

19. An oral dosage form comprising: an inner core comprising an outer surface and at least one therapeutic agent; and at least one filament extending from at least a portion of the outer surface of the inner core, the filament capable of transitioning between a first, non-gripping position and a second tissue-gripping position.

20. The oral dosage form of claim 1, wherein the oral dosage form maintains the ability to engage different gastrointestinal tissues while being passed through the gastrointestinal tract.

* * * * *